United States Patent [19]  
Davison

[11] Patent Number: 4,657,858  
[45] Date of Patent: Apr. 14, 1987

[54] CLONING VECTORS COMPRISING A RESTRICTION SITE BANK AND THE CONSTRUCTION THEREOF

[75] Inventor: John R. N. Davison, Brussel, Belgium

[73] Assignee: Labofina, S.A., Brussels, Fed. Rep. of Germany

[21] Appl. No.: 609,550

[22] Filed: May 11, 1984

[30] Foreign Application Priority Data

May 11, 1983 [EP] European Pat. Off. ........ 83104665.1

[51] Int. Cl.$^4$ .................... C12P 21/00; C12N 15/00; C12N 1/00; C12N 1/20
[52] U.S. Cl. .................................. 435/68; 435/172.2; 435/317; 435/253; 935/22; 935/26; 935/27; 536/27
[58] Field of Search ............ 435/172.3, 68, 317, 435/253; 935/22, 26, 27; 536/27

[56] References Cited

U.S. PATENT DOCUMENTS 4,528,266 7/1985 Pieczenik .................. 435/6

OTHER PUBLICATIONS

Talmadge et al., 1980 "Construction of Plasmid Vectors with Unique Pst I Cloning Sites in a Signal Coding Region" *Gene* viz 235-241.

Rao et al., 1979 "Plasmid Pkc7: A vector Containing Ten Restriction Endonuclease Sites Suitable for Cloning DNA Segments" *Gene* v7 79-82.

*Primary Examiner*—Thomas G. Wiseman  
*Assistant Examiner*—Joanne M. Giesser  
*Attorney, Agent, or Firm*—Stephen A. Bent; John K. Abokhair; M. Norwood Cheairs

[57] ABSTRACT

Vectors are disclosed for cloning any foreign DNA in prokaryotic and eukaryotic organisms, which vectors comprise a restriction site bank containing a large number of unique restriction sites. The disclosed vectors permit the cloning of large DNA fragments and complete genes without the risk of unwanted DNA cleavage by restriction enzymes. Also disclosed are methods for preparing the aforementioned vectors and processes using the vectors for the cloning of DNA, for the production of polypeptides, and the like.

43 Claims, 6 Drawing Figures

CLONING VECTORS COMPRISING A RESTRICTION SITE BANK AND THE CONSTRUCTION THEREOF

BACKGROUND OF THE INVENTION

The present invention relates to vectors containing a small DNA segment called a "restriction site bank" which comprises a large number of unique cloning sites and which permits the cloning of any foreign DNA material into prokaryotic and eukaryotic cells. The invention also relates to processes for the construction of restriction site banks and to the use of vectors containing such restriction site banks.

It is well known that restriction enzymes play a key role in recombinant DNA technology, e.g., in the generation of complementary cohesive ends for a cloning vector and for the DNA to be cloned, thus allowing for the recombination of the vector and DNA. A large number of such restriction enzymes which recognize specific, well-defined sites are now available, providing great versatility in cloning experiments, but only when the corresponding sites are present in the vector of choice. Moreover, these sites should be present in limited number and should preferably be unique, so as to reduce as much as possible the number of recombination events necessary to obtain the desired recombinant DNA.

Previous development of plasmid vectors for cloning into prokaryotes has concentrated on the use of multiple antibiotic resistance genes containing unique restriction sites, so that cloning at one of these sites results in sensitivity to an antibiotic (insertional inactivation), thereby facilitating detection of recombinants. While extremely useful, this approach has its limitations. First, it is difficult to construct a plasmid containing a large number of unique restriction sites since addition of other antibiotics resistance genes introduces duplicates sites and at the same time leads to an undesirable increase in plasmid size. Second, there are many situations in which insertional inactiviation is not useful, e.g., when screening for specific rare recombinants in shotgun experiments, or when a suitable unique cloning site in an antibiotic resistance gene is not available. In the case of eukaryotes, the use of plasmid vectors with multiple antibiotic resistance genes is of little interest, as eukaryotic cells are generally resistant to most antibiotics.

Because of these limitations, techniques have been developed which allow screening for hybrid colonies in other ways, e.g., by using hybridization probes, by complementation of genetically distinguishable host strains, or by simply screening a large number of plasmid DNA preparations using restriction enzymes. Similarly, the proportion of nonrecombinant, parental-type plasmids can be reduced by alkaline phosphatase treatment of the vector prior to ligation, or by the cloning of fragments between two different noncomplemetary restriction sites.

SUMMARY OF THE INVENTION

For these reasons, the present invention eschews insertional inactivation as a principal consideration in plasmid construction, but rather embodies a different concept, namely, that of the restriction site bank. A "restriction site bank" is defined herein as a segment of DNA specifically designed to be small in size and to have a maximum number of unique restriction sites. According to this definition, any subdivision or addition to a restriction site bank also results in a restriction site bank.

According to the present invention, vectors are provided which contain a larger number of unique restriction sites than conventional vectors, preferably at least 10 unique restriction sites selected from the group consisting of EcoRI, ClaI, HindIII, EcoRV, BamHI, SphI, SalI, SalI (AccI, HincII), XmaIII, NruI, SacI, KnpI, AsuII, PstI, BclI, BglII, XbaI, PvuII, BalI, MstII, AvaI, and XhoI. The vectors of the present invention allow the cloning of DNA, including complete genes, without running the risk of cleaving the DNA to be cloned by a corresponding restriction enzyme. Furthermore, several genes can be cloned simultaneously with vectors of the present invention.

Other objectives, features, and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Preferred embodiments of the present invention are described in detail below with reference to the drawings in which.

DETAILED DESCRIPTION OF PREFERRED EMBODIMENTS

Figure 1:
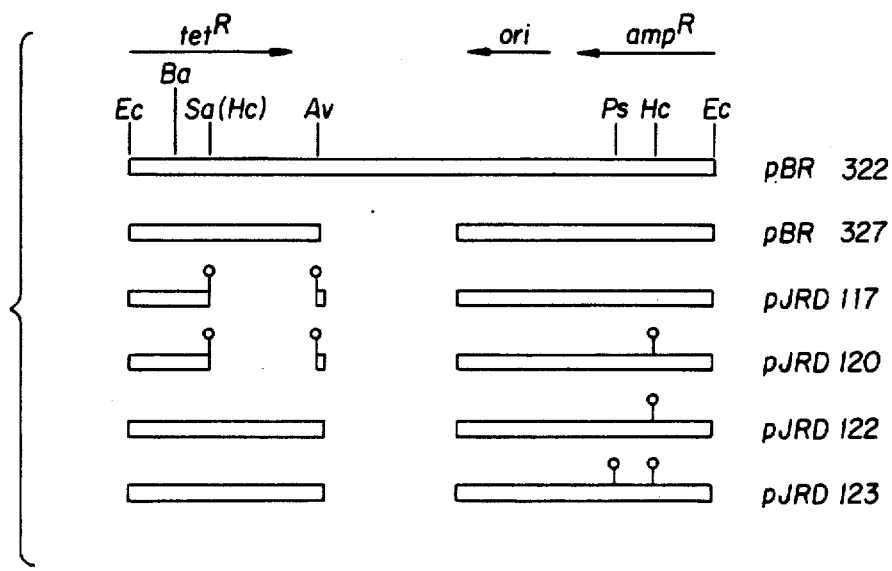
FIG. 1 shows a schematic view of the replication segment of a vector according to the present invention.

In accordance with one preferred embodiment of the present invention, a vector is provided for cloning any foreign DNA material in prokaryotic and eukaryotic organisms, which vector contains a restriction site bank b1 derived from the HindIII-AvaI region of the bacteriophage T5 HindIII-L fragment. The vector comprises unique sites for the restriction enzymes HindIII, SacI, KnpI, AsuII, PstI, BglII, XbaI, HincII, PvuII, BalI, MstI and AvaI, arranged in the indicated order.

From this vector other vectors can be derived by modification of the above-described restriction site bank b1. Thus, the present invention also provides a vector wherein restriction sites for enzymes XmaIII and BclI have been added to bank b1 by replacing the 910 bp PstI-BglII segment thereof by the 210 bp PstI-BglII fragment from plasmid pKC7. The resulting restriction site bank, referred to hereinafter as b2, therefore comprises unique cloning sites for restriction enzymes HindIII, SacI, KpnI, AsuI, PstI, XmaIII, BclI, BglII, XbaI, HincII, PvuII, BalI, MstII and AvaI, arranged in the indicated order.

The present invention further provides vectors derived from those described above by fusing the HindIII ends of restriction site banks b1 and b2, respectively, to the AvaI end of the EcoRI-AvaI fragment from plasmid pBR322, thus introducing additional cloning sites for the restriction enzymes EcoRI, ClaI, HindIII, EcoRV, BamHI, SphI, SalI (AccI, HincII), XmaIII and NruI arranged in the indicated order. The new restriction site banks thus constructed will be referred to hereafter as b3 (if derived from b1) or b4 (if derived from b2).

Restriction site banks b3 and b4 contained in the above-mentioned vectors comprise two HincII sites, one of which is preferably absent. Accordingly, the present invention also provides vectors containing a modification of banks b3 and b4. The restriction site bank thus modified will be referred to hereinafter as b5 or b6, according to whether it is derived from b3 or b4, respectively.

Similarly, restriction site banks b4 and b6 comprise two XmaIII sites, one of which is also preferably absent. Thus, the present invention also provides vectors containing a modification of banks b4 or b6, comprising a unique XmaIII site derived from the pBR322-derived portion thereof. The restriction site bank thus modified will be referred to hereinafter as b7 and b8, according to whether it was derived, respectively, from b4 or b6.

To further increase the number of useful restriction sites available for cloning, there is also provided, in accordance with the present invention, vectors derived by introducing a XhoI site at the AvaI end of the restriction site bank of any of the previously described vectors. In the case of restriction site b8, for example, the new restriction bank thus formed comprises the following cloning sites for restriction enzymes: EcoRI, ClaI, HindIII, EcoRV, BamHI, SphI SalI (AccI, HincII), XmaIII, NruI, SacI, KpnI, AsuII, PstI, BclI, BglII, XbaI, PvuII, BalI, MstII, and XhoI, arranged in the indicated order.

To increase still further the number of unique restriction sites available for cloning, there is additionally provided, in accordance with the present invention, vectors wherein the ScaI site between the tet$^R$ gene and the SacI site within the pBR322-derived region is removed, thus leaving a unique ScaI site in the amp$^R$ gene.

In accordance with another aspect of the present invention, there are provided processes for the construction of the restriction site banks contained in the vectors as described above. In accordance with one preferred embodiment of the present invention, the process for the construction of restriction site bank b1, comprising unique cloning sites for the restriction enzymes HindIII, SacI, KpnI, AsuII, PstI, BglII, XbaI, HincII, PvuII, BalI, MstII and AvaI, arranged in the indicated order, comprises the steps of:

(a) generating a single XbaI site by deleting the segment between the two XbaI sites of the HindIII-AvaI region of the bacteriophage T5 HindIII-L fragment; and (b) generating a single BglII site and simultaneously removing the redundant PvuII site by deleting the 1250 bp segment between the two BglII sites present in the same region.

From this first restriction site bank b1, further banks can be generated. For instance, restriction site bank b2 can be constructed in accordance with the present invention by a process wherein excess DNA material present in restriction site bank b1 is removed by replacing the 910 bp PstI-BglII segment of the latter with a 210 bp PstI-BglII fragment from plasmid pKC7, resulting in the addition of sites for the restriction enzymes XmaIII and BclI.

Still other restriction site banks comprising more cloning sites than provided by b1 and b2 can be constructed therefrom in accordance with the present invention by fusion with a DNA fragment from plamsid pBR322. Thus, according to one preferred embodiment of the present invention, the HindIII end of the restriction site bank b1 is fused with the AvaI end of the EcoRI-AvaI fragment from plasmid pBR322. This fusion results in restriction site bank b3, comprising additional cloning sites for the restriction enzymes EcoRI, ClaI, HindIII, EcoRV, BamHI, SphI, SalI (AccI, HincII), SmaIII and NruI, arranged in the indicated order. According to another preferred embodiment, the HindIII end of the restriction site bank b2 is similarly fused with the AvaI end of the aforementioned pBR322 fragment, resulting in a restriction site bank b4 containing the same additional cloning sites as in bank b3. The same restriction site bank b4 can also be constructed according to the present invention by a process wherein restriction site bank b3 is used and a DNA segment present in restriction site bank b1 is removed as described above for the construction process of restriction site bank b2.

Restriction site bank b3 has two sites for the enzyme HincII: one in the pBR322-derived fragment and the other in the bacteriophage-derived region. From this restriction site bank, bank b5 can be constructed, containing a unique site for HincII. In accordance with the present invention, this is achieved by a process wherein the HincII site in the BglII-AvaI region of restriction site bank b1 is deleted while retaining the adjacent XbaI and PvuII sites, and the resulting deleted region is then substituted for the BglII-AvaI region of restriction site bank b3.

Similarly, restriction site bank b6, containing a unique HincII site, can be constructed in accordance with the present invention by substituting the above-mentioned deleted region from bank b1 for the BglII-AvaI region of restriction site bank b4. The same restriction site bank b6 can also be constructed according to the present invention by a process wherein restriction site bank b5 is used and a DNA segment present in restriction site bank b1 is removed as described above for the construction process of restriction site bank b2.

Restriction site bank b4 has two XmaIII sites: one in the pBR322-derived region and the other in the pKC7-derived fragment. According to another embodiment of the present invention, the latter XmaIII site is deleted, resulting in restriction site bank b7.

Similarly, the same XmaIII site can be deleted from restriction site bank b6, resulting in a restriction site bank b8 which contains unique sites for the restriction enzymes EcoRI, ClaI, HindIII, EcoRV, BamHI, SphI SalI (AccI, HincII), XmaIII, NruI, SacI, KpnI, AsuII, PstI, BclI, BglII, XbaI, PvuII, BalI, MstII and AvaI, arranged in the indicated order. The same restriction site bank b8 can also be constructed from bank b7 according to the present invention by a process wherein the HincII site in the BglII-AvaI region of restriction site bank b1 is deleted and the resulting deleted region is then substituted for the BglII-AvaI region of the restriction site bank b7.

From any of the preceding restriction site banks still other banks may be generated, all in accordance with the present invention. For instance, according to one embodiment of the present invention, a XhoI site is fused to the AvaI end of any of the above-described restriction site banks b1 to b8, thus destroying the original AvaI site but leaving a new XhoI site which AvaI also cleaves.

It is an important feature of the present invention that the restriction site banks constructed as described above can be incorporated into any cloning vehicle, whatever the host organism. Thus, they can be inserted into vector systems designed for cloning and expressing genes in prokaryotic organisms such as *Escherichia coli, Bacillus subtilis*, and Pseudomonas species, or in eukaryotic organisms like yeast, fungi, and even animal and plant cells. In these different hosts, the large number of unique restriction sites afforded by the restriction site banks of the present invention provides exceptional cloning versatility, and the clustering of such sites facilitates subsequent operations, including cloning and deletion analysis of large cloning fragments. Incorporated into vectors which allow the cloning of large fragments, such as cosmids, the restriction site banks of the present invention are especially useful for the construction of genomic libraries.

One method for using the restriction site banks in accordance with the present invention is to incorporate them into a plasmid vector carrying both (a) an origin of replication recognized by the replication machinery of the selected host and (b) a gene imparting to the host resistance against some drug, e.g., an antibiotic, or a gene complementing some auxotrophy of the host for an essential metabolite, e.g., an amino acid, so as to allow efficient screening of transformed organisms. Most plasmids currently usef for transforming prokaryotic organisms, especially *E. coli*, can be used for this purpose. Examples of such plasmids are pBR322 and other related plasmids such as pBR327, pMB9, etc. Other plasmids, such as the natural replicon ColEI and related or unrelated plasmids like P15A, F, RSF1010, and R616, can also be used to design efficient vectors containing restriction site banks in accordance with the present invention. Similarly, plasmids used for the transformation of eukaryotic organisms may be used. Typical examples of such plamsids are those designed for the transformation of yeast, e.g., pJDB207, pJDB219, and pMp78.

In carrying out a stepwise process for the construction of restriction site banks according to the present invention, the DNA fragment containing clustered cloning sites which is obtained after each step must be produced and isolated in amounts sufficient for further processing. This can be accomplished by inserting the DNA fragment into a plasmid vector like those referred to above and transforming a selected host with the resulting chimeric plasmid. Although any microorganism capable of being transformed by exogenous DNA can be used for this purpose, *E. coli* is a preferred host, since well-designed and efficient methods are available not only for the transformation of *E. coli* but also for DNA amplification and recovery. In the following examples, the *E. coli* strain MM294 is used as a host, unless otherwise indicated.

In general, the currently available DNA segments that permit replication and selection in the variety organisms previously indicated are not directly suitable for incorporation of the above-described restriction site banks, and therefore require prior modification. A typical procedure for such modification is given in the following examples, which should be considered as illustrative only and not limiting on the present invention.

EXAMPLE 1

Modification of the replication segment and selective marker

In this example, the vector used for the replication of the restriction site bank under construction was derived by modification of plasmid pBR327, itself obtained from pBR322 by EcoRII deletion (Soberon et al., "Construction and characterization of new cloing vehicles, IV. Deletion derivatives of pBR322 and pBR325," *Gene* 9: 287–305, 1980). The modification of pBR327 comprised removing from the $amp^R$ gene the PstI and HincII sites, resulting in the presence of unique PstI and HincII sites in the final restriction site bank used for cloning. (Failure to remove these sites would prevent cloning by inactivation of the $amp^R$ selective marker.) The unique PvuI and ScaI sites in the $amp^R$ gene were not removed, since they were not provided in the final restriction site bank and might be useful to certain types of recombinant constructions. The procedure followed is shown in FIG. 1. The HincII site in the $tet^R$ gene of pBR327 was removed by fusing the unique SalI and AvaI sites, producing the tetracycline sensitive plasmid pJRD117. The now-unique HincII site in the $amp^R$ gene was then removed by mutagenesis, followed by repeated cycles of DNA isolation, restriction cleavage and transformation using the method of Talmadge and Gilbert ("Construction of plasmid vectors with unique PstI cloning sites in a signal sequence coding region," *Gene* 12: 235–241, 1980). This resulted in plasmid pJRD120, which had lost the unique HincII site while retaining $amp^R$. The region EcoRI-PstI of pBR327 (coordinates 3271–2523) was then restored to pJRD120 to give $amp^R$-$tet^R$ plasmid pJRD122, which contained a unique HincII site. pJRD122 was then subjected to further mutagenesis and restriction-transformation cycles, resulting in the selection of pJRD123, which is $amp^R$ and $tet^R$, has a unique HincII site, and lacks a PstI site, but retains β-lactamase activity.

The above-described procedure resulted in an additional mutation which caused a GC-to-AT base pair change at the position corresponding to coordinate 3132 of pBR322. This mutation had two important effects. First, it increased the copy number of the plasmid from about 30 to 120, so that a cloned gene would be better expressed due to increased gene dosage. Second, it altered the normal incompatibility mechanism of the plasmid, which was then able to coexist side by side in the same cell as pBR322 and its derivatives (two pBR322 type plasmids cannot normally do this). The advantage of this is that it was then possible to introduce different genes cloned on different plasmids into the same cell. A similar mutation has previously been independently described ("Plasmid ColEI incompatibility determined by interaction of RNA I with primer transcript," Tomizawa & Itoh, *Proc. Natl. Acad. Sci. USA* 78: 6091–6100, 1981).

Construction of the restriction site bank

The basis for the construction of a restriction site bank in accordance with the present invention is the HindIII-L fragment from bacteriophage T5. This fragment contains restriction sites for SacI, KpnI, BglII, XbaI and PvuII, none of which enzymes cleave plasmid pBR327. However, the aforementioned T5 fragment is too large (3.9 kb) for use in vector construction, so deletions are necessary to remove excess DNA and unwanted restriction sites.

Figure 2A:
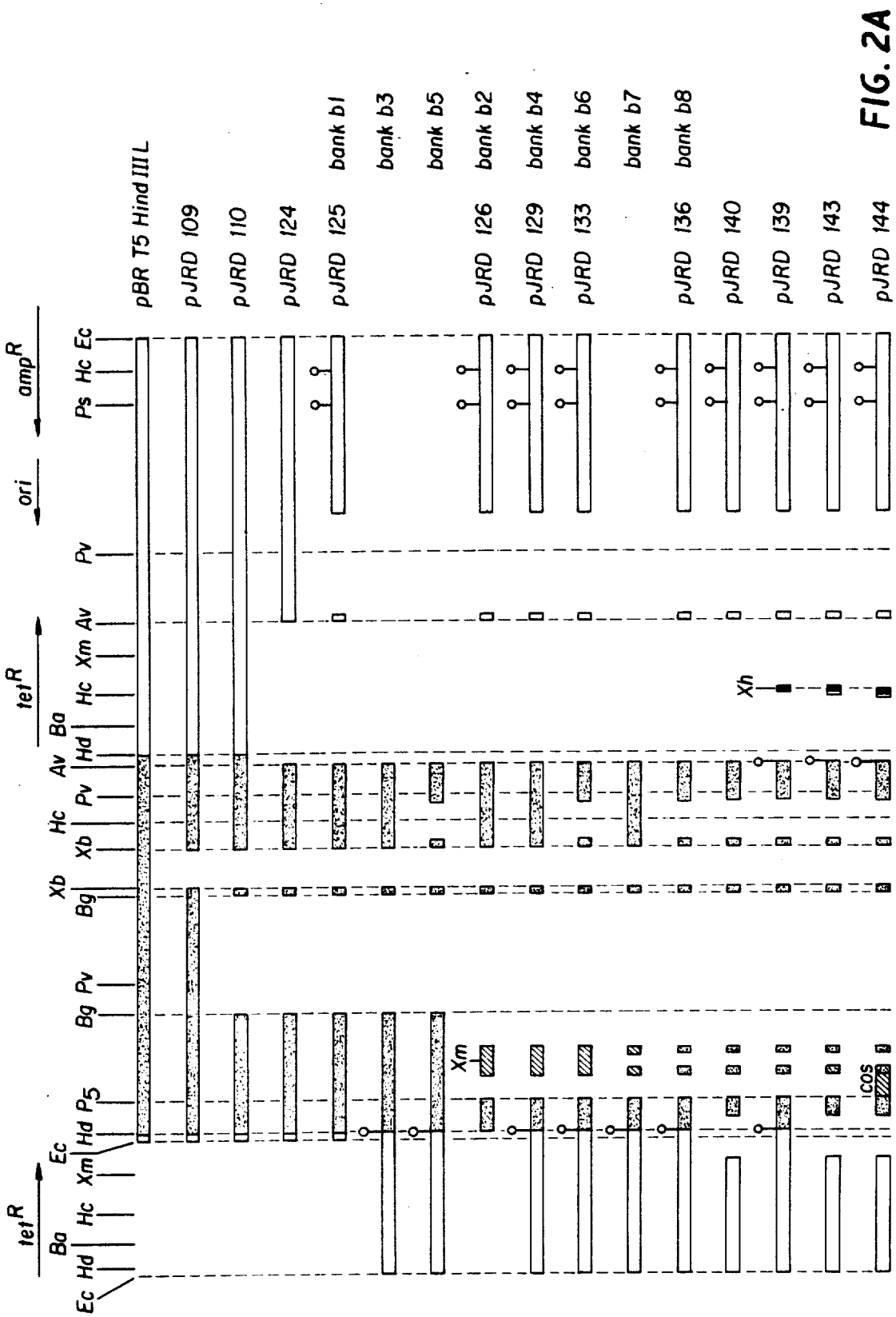
FIGS. 2a and 2b present schematic views of restriction site banks of the present invention.
Figure 2B:
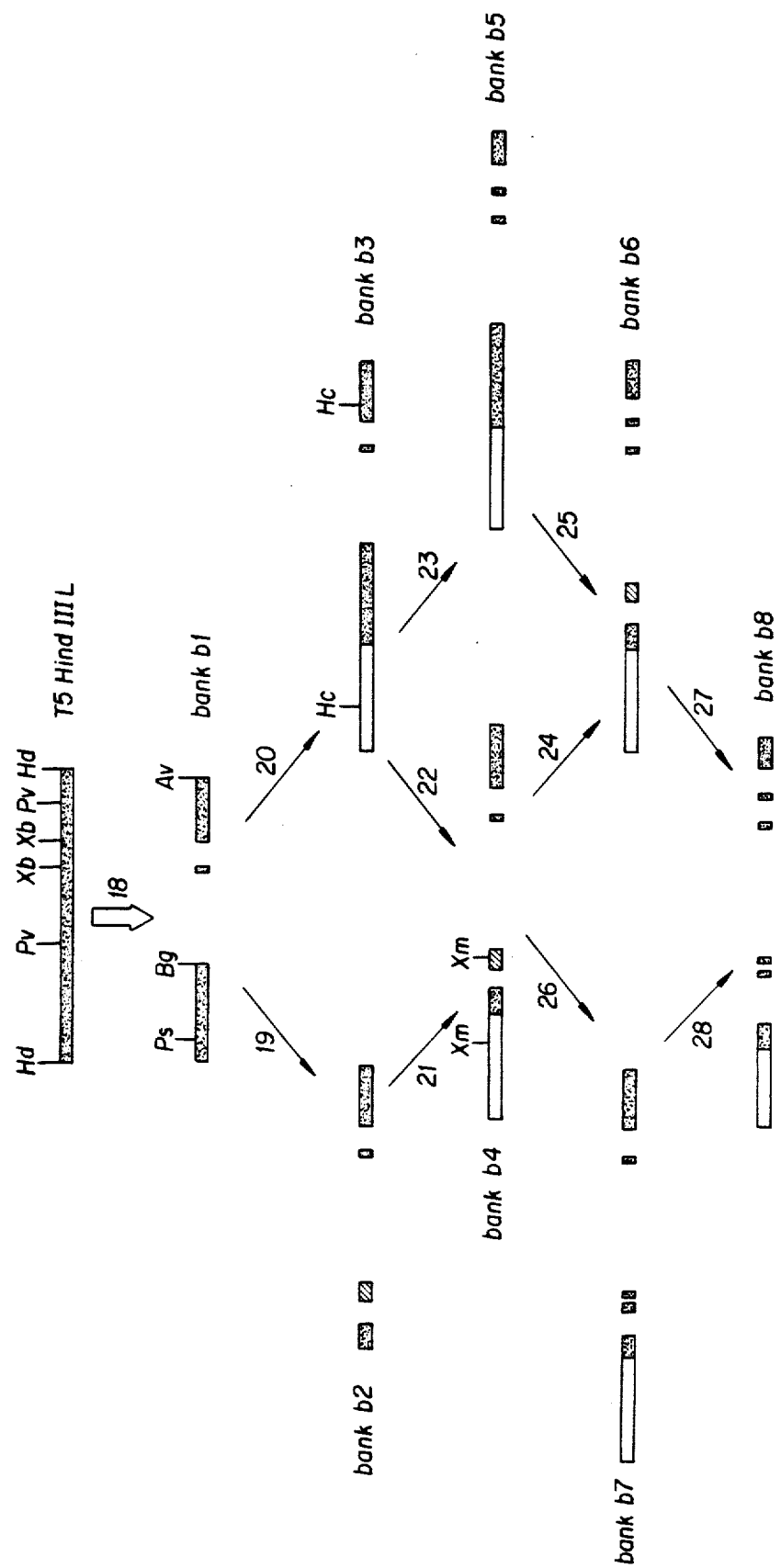

FIGS. 2a and 2b illustrate a typical procedure, which begins with the initial insertion of the HindIII-L fragment from bacteriophage T5 into plasmid vector pBR322 (Brunel et al., "Cloning of bacteriophage T5 DNA fragments in plasmid pBR322 and bacteriophage λgtWES," Gene 8: 53–68, 1979). First, the 490 bp region between the two XbaI sites of the fragment was removed to generate a single XbaI site (FIG. 2, pJRD109). Second, the 1250 bp BglII-BglII region was removed to generate a single BglII and, simultaneously, to delete an unwanted PvuII site (FIG. 2, pJRD110). Third, the 1405 bp AvaI-AvaI fragment was deleted, removing one of the two AvaI sites of plasmid pJRD110, one of the two HindIII sites, and the entire $tet^R$ region (the latter was not expressed due to the insertion of the original HindIII-L fragment in the $tet^R$ promoter), to give plasmid pJRD124 (FIG. 2).

The region AvaI-HindIII of the latter plasmid was then replaced by the corresponding region of the plasmid pJRD123 constructed as described above (FIG. 1). This replacement simulatenously introduced the Eco RII deletion of pBR327, the $amp^R$ region of pJRD123 carrying the Pst° and Hinc° mutations, and the increased copy number mutation, to give plasmid pJRD125 (FIG. 2). The 910 bp PstI-BglII region of this latter plasmid was then replaced by a 210 bp PstI-BglII fragment from plasmid pKC7 (Rao & Rogers, "Plasmid pKC7: A vector containing ten restriction endonuclease sites suitable for cloning DNA segments," Gene 7: 79–82, 1979), thus removing excess DNA and introducing a BclI site and a XmaIII site, resulting in plasmid pJRD126 (FIG. 2).

Plasmid pJRD126 is sensitive to tetracycline due to deletion of the entire HindIII-AvaI region of pBR322. (coordinates 29–1424). This region contains several unique restriction sites that can be used for insertional inactivation and therefore can advantageously be included in a restriction site bank according to the present invention. The aforementioned HindIII-AvaI region was therefore reintroduced into pJRD126, resulting in plasmid pJRD129. To do this, the DNA of plasmid pBR322 was cleaved with AvaI, was repaired using a DNA polymerase I Kleenow fragment and deoxynucleoside triphosphates, and then was cleaved with EcoRI. Simultaneously, the DNA of pJRD126 was cleaved with HindIII, was repaired with a DNA polymerase I Kleenow fragment and deoxynucleoside triphosphates, and then was cleaved with EcoRI. The two plasmids were then mixed and ligated, resulting in replacement view a cohesive-end-blund-end ligation of the EcoRI-HindIII region of pJRD126 with EcoRI-AvaI region of pBR322, destroying both the HindIII site of pJRD126 and the AvaI site of pBR322. The resulting plasmid pJRD129 was $amp^R$, $tet^R$ and had one unique HindIII site and one unique AvaI site.

Plasmid pJRD129 has unique restriction sites for most restriction enzymes of interest but has two for HindII: one located in the $tet^R$ region and the other in the 500 bp XbaI-PvuII fragment which contains no other sites of interest. This latter site and the adjacent excess DNA was removed by HincII digestion of pJRD126 (which has a unique HincII site), followed by digestion with nuclease Bal 31 and blunt-end ligation. The resulting plasmids were screened for retention of both the XbaI and PvuII fragment (pJRD130). The deletion variant was then transferred to plasmid pJRD129 by digestion of both plasmids with BglII+A val followed by ligation and transformation, resulting in plasmid pJRD133.

Plasmid pJRD133 has two sites for restriction enzyme XmaIII; one located in the $tet^R$ region and the other in the 210 bp PstI-BglII region introduced from pKC7 as explained above. This region contains three HpaII fragments, one of which carries the XmaIII site. The isolated PstI-BglII region was therefore digested with HpaII and the products ligated into the PstI-BglII cleaved pJRD133 vector, using the method of Heusterspreute and Davison ("A method for the generation of small pre-determined deletions in plasmid DNA: Deletion analysis of the $tet^R$ region of vector pBR322," Gene, 23, 1983, pp 35–40). The resulting plasmid pJRD133 lacked all three HpaII fragments (127 bp) and contained a unique XmaIII site in the $tet^R$ region.

Plasmid pJRD136 has unique sites for virtually all commonly used restriction enzymes recognizing a 6 bp sequence, but lacks sites for XhoI. A DNA linker carrying a XhoI site was therefore introduced into the AvaI site of pJRD136. (This site is not particularly useful for cloning, since AvaI has four possible recognition sites.) Introduction of the linker was accomplished by repairing an AvaI-cleaved pJRD136, using a DNA polymerase Kleenow fragment, followed by blunt-end ligation of the linker, giving pJRD139. This procedure destroys the original AvaI site, but, AvaI also cleaves the new XhoI site.

Figure 3:
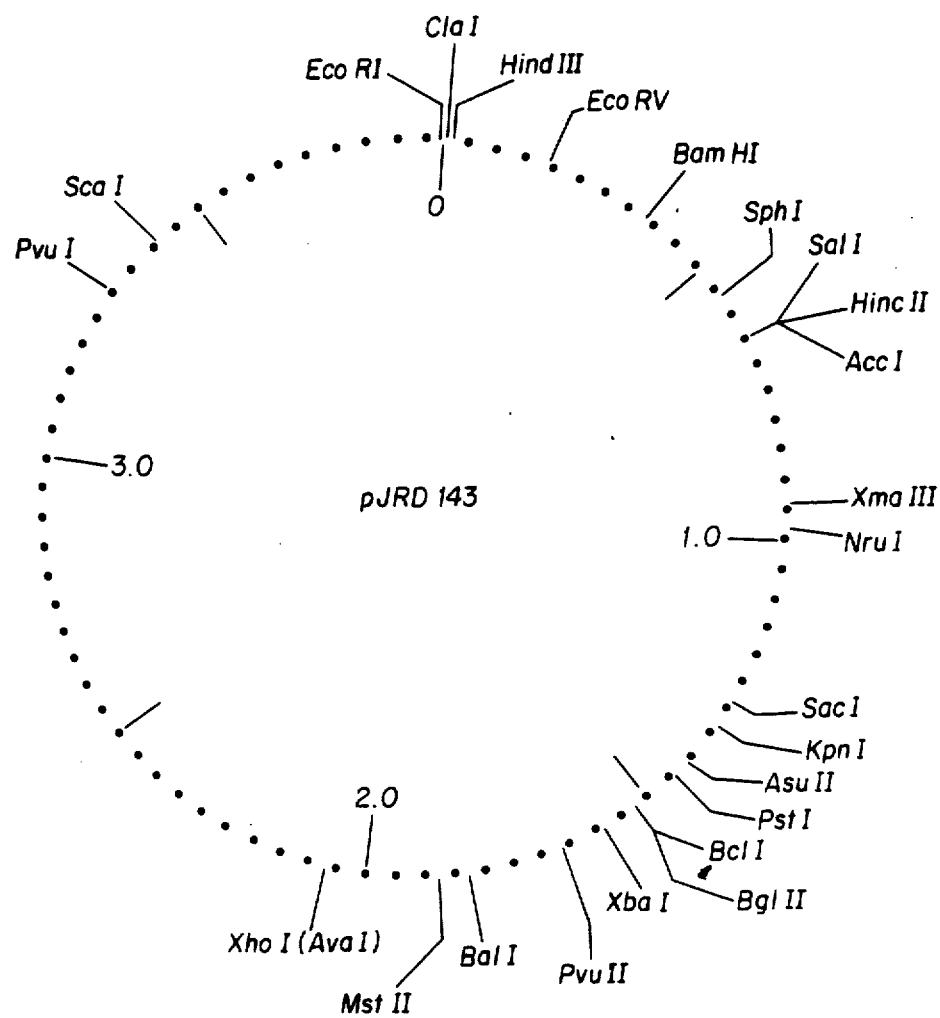
FIG. 3 gives a detailed restriction map of a plasmid vector obtained in accordance with the present invention.

Finally, an unwanted region of about 280 bp (containing an unwanted ScaI site) between the end of the $tet^R$ gene and the SacI site was removed. The small SalI-KpnI fragment of pJRD136 was separated from the large SalI-KpnI fragment and subdigested by TaqI and RsaI, followed by religation to the large fragment using the techniques of Nilsson and Magnusson, "Sealing of gaps in duplex DNA by T4 DNA ligase," Nucl. Acids Res. 10: 1425–1437 (1983) and Heusterspreute and Davison, supra. This deletion removed the four terminal amino acids codons of the $tet^R$ gene and replaced them with a single amino acid codon immediately followed by a nonsense codon. The resulting plasmid (pJRD140) showed normal resistance to tetracycline. The deletion was then transferred to plasmid pJRD139 by replacing the HindIII-PstI region, resulting in plasmid pJRD143 (see FIG. 3), which contains a unique ScaI site.

EXAMPLE 2 pJRD144—a cosmid variant of pJRD143 (see FIG. 2)

The vector pJRD143 is a small, multicopy plasmid very useful for the cloning of small DNA molecules (10 kb). A culture of E. coli strain MM294 transformed with the plasmid pJRD143 has been deposited at the Centraalbureau voor Schimmelscultures, Baarn, Netherlands, on May 11, 1983, under file number LMD 83.07–CBS 396-83.

An intrinsic difficulty with vectors like pJRD143 is that they do not transform particularly well ($2 \times 10^5$ clones μg of DNA) and that, moreover, transformation becomes increasingly inefficient when they carry large DNA inserts. Consequently, large numbers of clones must be screened for a desired gene, and the successful cloning of the desired gene is less likely because of the preferential cloning of small DNA fragments. A solution to these difficulties is the use of cosmids, which are small plasmids containing the cos sites of bacteriophage λ required for packaging of DNA into capsids. Cosmids permit the high efficiency transfer of very large DNA molecules to *E. coli*, where they are maintained as plasmids.

The cos region of λ, contained in the 400 bp PstI-PstI fragment of MUA 10 (Meyerowitz et al, "A new cosmid vector and its use," Gene 11: 271-282 (1980) was therefore introduced into pJRD143 at the plasmid's unique PstI site. The resulting cosmid pJRD144 combines the restriction site bank and high copy number advantages of pJRD143 with the cosmid properties of MUA10 mentioned above. Cosmid pJRD144 allows all of the sites of pJRD143 to be used for cloning (except PstI) and is particularly efficient for the subsequent subcloning and deletion anaylsis of the large cloned DNA fragment.

EXAMPLE 3

Construction of an *E. coli*—yeast shuttle plasmid

*Saccharomyces cerevisiae* is an important organism for both fundamental and applied science, and plasmids have been constructed that are able to replicate in both *S. cerevisiae* and *E. coli*, using the origin of replication of the yeast 2μ plasmid and the origin of replication of pBR322, respectively Beggs, "Multiple-copy yeast plasmid vectors," IN MOLECULAR GENETICS IN YEAST (Alfred Benson Symposium No. 16) 383-395 (D. von Wettstein et al eds. 1981)). Such yeast vectors can be advantageously modified, in accordance with the present invention, by the introduction of additional unique cloning sites like those found in pJRD143.

Modification of the replication segment

The vector pJRD207 comprises three different DNA segments: a fragment of yeast plasmid 2μ, responsible for DNA replication in yeast; the LEU 2 gene of yeast, which permits plasmid selection and maintenance in a LEU 2 yeast autotroph; the plasmid pAT153, a deletion derivative of pBR322 resembling pBR327 (Twigg and Sherratt, "Trans-complementable copy-number mutants of plasmid ColEI," Nature 283: 216-218 1980). The region 2μ-LEU 2 requires little modification, since it has relatively few restriction sites which are located in regions essential for either selection or replication.

The XbaI site in pJDB207 is located in the origin of replication for the 2μ plasmid. The XbaI site was removed by end-filling with DNA polymerase I, followed by blunt-end ligation and transformation. The resulting plasmid (pJDB207 XbaI°) lacked the XbaI site but was unchanged in its ability to transform and replicate in yeast.

Insertion of the restriction site bank into pJDB207 XbaI°

Figure 4:
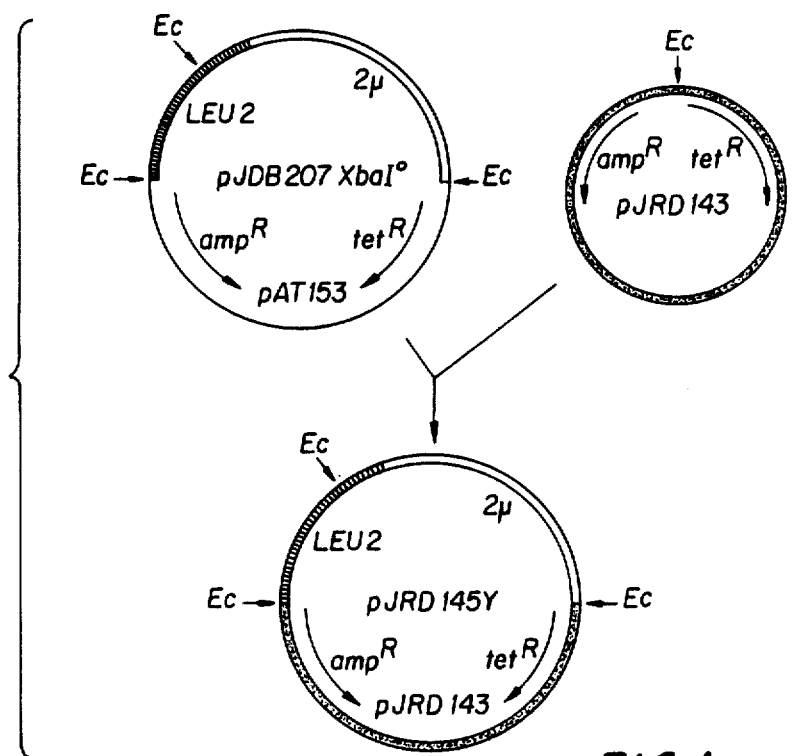
FIG. 4 shows a schematic view of a yeast plasmid containing a restriction site bank of the present invention.

Thereafter the entire plasmid pJRD143 was inserted into pJDB207 XbaI° by EcoRI digestion and ligation, thus exactly replacing the pAT153 plasmid. The resulting plasmid pJRD145Y (FIG. 4) had all of the unique restriction sites of pJRD143 except KpnI (two sites present) and EcoRI (three sites present). At the same time, the plasmid retained the unique HpaI and BstEII sites of pJDB207.

EXAMPLE 4

Construction of another *E. coli*-yeast shuttle cosmid

Construction of a second *E. coli*-yeast shuttle cosmid was achieved by replacing the SalI-BglII region of pJRD145Y with that of pJRD144, thereby introducing the cos site. The resulting cosmid pJRD146Y had all of the combined advantages of pJRD144 and pJRD145Y, in that it was able to grow and to be selected in both *E. coli* and yeast, and it could be packaged in bacteriophage capsids to permit very high efficienty of cloning in *E. coli*+.

EXAMPLE 5

Construction of a vector of wide host range incorporates a restriction site bank The replication of plasmids based solely upon the pMBI replication (e.g., pMB9, pBR322, and all of their derivatives, including those described above) is restricted to *E. coli* and its close relatives, so that cloning in other bacterial species is impossible. In contrast, other plasmids are known that are able to replicate in a wide variety of gram negative bacteria, including *Escherichia coli, Pseudomonas aeruginosa, Pseudomonas putida, Agrobacterium tumifaciens, Rhijobium meloti, Acetobacter xylinium, Azotobacter vinelandii, Alicagenes eutrophus, Rhodopseudomonas spheroides,* and *Methylophilus methylotrophus.* The wide-host-range plasmid which is the most promising as a cloning vector is RSF1010, which has a high copy number and relatively small size, but RSF1010 suffers the disadvantage of having very few unique restriction sites. (Nagahari and Sakaguchi, 1978). Accordingly, the non-essential EcoRI-PstI region containing the gene for resistance to sulphonamides was replaced by the EcoRI-XhoI region of pJRD143, this operation being facilitated by the addition of a XhoI linkers at the PstI site of RSF1010. The resulting plasmid (pJRF202 P) contained the entire restriction site bank of pJRD143 and was resistant to tetracycline and streptomycin. Most of the restriction sites except for SacI were unique.

It will be appreciated from the foregoing description that the present invention also provides a method for producing a polypeptide for which a corresponding DNA segment is available. Thus, in accordance with the present invention, a DNA segment coding for a polypeptide would be inserted at a restriction site in a suitable vector comprising any one of the above-described restriction site banks. The site would have been selected so that cleavage of the DNA segment by a restriction enzyme recognizing the restriction site is avoided. To ensure transcription of the DNA segment after transformation of a suitable cell with the vector, a promoter on some other transcription control sequence could be inserted at a second restriction site in the restriction site bank which is located upstream from the first site, relative to the direction of the transcription. Transformed cells could then be cultured to produce useful quantities of the polypeptide.

What is claimed is:

1. A cloning vehicle comprising a restriction site bank which is the product of a process comprising the steps of (1) digesting the T5 phage genome with HindIII endonuclease into a plurality of fragments and (2) isolating from said plurality the HindIII-L fragment, said restriction bank comprising a first sequence, in the following order, of sites for the restriction enzymes Hin dIII, Z, KpnI, AsuII, PstI, BglII, XbaI, F, PvuII, BalI, MstII and G, where Z denotes either a SacI site or a DNA segment lacking a site for a restriction enzyme, F denotes either a HincII site or a DNA segment lacking a site for a restriction enzyme, and G denotes an AvaI site or a XhoI site.

2. A cloning vehicle according to claim 1, wherein F denotes a HincII site and said restriction site bank further comprises, in the following order, one site for each of the restriction enzymes XmaIII and BclI between said PstI site and said BglII site in said first sequence, such that said XmaIII site follows said PstI site in said restriction site bank.

3. A cloning vehicle according to claim 2, wherein said XmaIII site and said BclI site are derived from a 210 base-pair PstI-BglII fragment of plasmid pKC7.

4. A cloning vehicle according to claim 1, wherein said restriction site bank further comprises a second sequence, in the following order, of sites for the restriction enzymes EcoRI, ClaI, HindIII, EcoRV, BamHI, SphI, C, D, and NruI, where
  C denotes one site selected from the group consisting of SalI, AccI, and HincII, and
  D denotes an XmaIII site or a DNA segment lacking a site for a restriction enzyme.

5. A cloning vehicle according to claim 4, wherein said second sequence of sites is derived from a EcoRI-AvaI fragment of plasmid pBR322.

6. A cloning vehicle according to claim 2, wherein said restriction site bank further comprises a second sequence, in the following order, of sites for the restriction enzymes EcoRI, ClaI, HindIII, EcoRV, BamHI, SphI, C, D, and NruI, where
  C denotes one site selected from the group consisting of SalI, AccI, and HincIi, and
  D denotes an XmaIII site or a DNA segment lacking a site for a restriction enzyme.

7. A cloning vehicle according to claim 6, wherein said second sequence of sites is derived from a EcoRI-AvaI fragment of plasmid pBR322.

8. A cloning vehicle according to claim 4, wherein F denotes a DNA segment lacking a site for a restriction enzyme and C denotes a HincII site.

9. A cloning vehicle according to claim 1, wherein
  (a) F denotes a DNA segment lacking a site for a restriction enzyme; and
  (b) said restriction site bank further comprises,
    (i) in the following order, one site for each of the restriction enzymes XmaIII and BclI between said PstI site and said BglII site in said first sequence, such that said XmaIII site follows said PstI site in order, and
    (ii) a second sequence, in the following order, of sites for the restriction enzymes EcoRI, ClaI, HindIII, EcoRV, BamHI, SphI, HincII, D, and NruI,
where D denotes an XmaIII site or a DNA segment lacking a site for a restriction enzyme.

10. A cloning vehicle according to claim 8, wherein D denotes a DNA segment lacking a site for a restriction enzyme.

11. A cloning vehicle according to claim 9, wherein D denotes a DNA segment lacking a site for a restriction enzyme.

12. A cloning vehicle according to claim 1, wherein G denotes a XhoI site.

13. A cloning vehicle according to claim 12, wherein F denotes a DNA segment lacking a site for a restriction enzyme.

14. A cloning vehicle according to claim 1, further comprising a DNA segment which contains a AvaI-HindIII region from plasmid pBR322 or a derivative thereof.

15. A cloning vehicle according to claim 14, wherein said region comprises a replication origin and the $amp^R$ gene of pBR322.

16. A cloning vehicle according to claim 1, further comprising a DNA segment which contains a modified region derived from the AvaI-HindIII region of plasmid pBR322 or a derivative thereof from pBR322, said modified region differing from said AvaI-HindIII region by at least one mutation selected from the group consisting of a mutation which increases the copy number of said cloning vehicle, a mutation which eliminates the HindII site from the $amp^R$ gene of said modified region, and a mutation which eliminates the PstI site from said $amp^R$ gene, said mutations in said $amp^R$ gene not destroying β-lactamase activity.

17. A cloning vehicle according to claim 16, wherein said modified region differs from said AvaI-HindII region by a GC-to-AT base pair change at a position in said modified region corresponding to coorrdinate 3132 of plasmid pBR322.

18. A cloning vehicle according to claim 16, wherein said modified region is derived from pJRD123.

19. A cloning vehicle according to claim 1, wherein
  (a) Z denotes a DNA segment lacking a site for a restriction enzyme, and
  (b) said cloning vehicle further comprises a DNA segment which contains a modified region derived from a HindIII-AvaI region of plasmid pBR322 or a derivative thereof, the AvaI site being removed and replaced by a XhoI site, said modified region differing from the preceding region by the deletion of a 280 bp segment between the $tet^R$ gene and a SacI site within said modified region
whereby the $amp^R$ gene of said modified region contains a unique ScaI site.

20. A cloning vehicle according to claim 1, further comprising a cosmid sequence.

21. A cloning vehicle according to claim 1, further comprising an origin of replication derived from yeast plasmid 2μ.

22. A cloning vehicle according to claim 21, said cloning vehicle being plasmid pJDB207.

23. A process for constructing a restriction site bank, comprising the steps of:
  (a) deleting a segment between the two XbaI sites in the HindIII-AvaI region of the HindIII-L fragment of the bacteriophage T5, thereby generating a unique XbaI site in said restriction site bank; and
  (b) deleting a 1250 bp segment between the two BglII sites in said HindIII-AvaI region, thereby generating a unique BglII site and removing one PvuII site in said restriction site bank,
whereby a restriction site bank is constructed which contains unique sites for the restriction enzymes HindIII, SacI, KpnI, AsuII, PstI, BglII, XbaI, HincII, PvuII, BalI, MstII and AvaI.

24. A process according to claim 23, further comprising after step (b) the step (c) of replacing a 910 bp segment between said PstI site and said BglII site in said restriction site bank with a 210 bp PstI-BglII segment derived from plasmid pKC7, whereby an XmaIII site and a BclI site are added to said restriction site bank.

25. A process according to claim 23, further comprising after step (b) the step (c) of fusing said restriction site bank at said HindIII site with the AvaI end of a EcoRI-AvaI segment derived from plasmid pBR322, whereby sites for the restriction enzymes EcoRI, ClaI, HindIII, EcoRV, BamHI, SphI, C, XmaIII and NruI are added to said restriction site bank, where C denotes SalI, AccI, or HincII.

26. A process according to claim 24, further comprising after step (c) the step (d) of fusing said restriction site bank at said HindIII site with the AvaI end of a EcoRI-AvaI segment derived from plasmid pBR322, whereby sites for the restriction enzymes EcoRI, ClaI, HindIII, EcoRV, BamHI, SphI, C, XmaIII and NruI are added to said restriction site bank, where C denotes SalI, AccI, or HincII.

27. A process according to claim 25, further comprising after step (c) the step (d) of replacing a 910 bp segment between said PstI site and said BglII site in said restriction site bank with a 210 bp PstI-BglII segment derived from plasmid pKC7, whereby an XmaIII site and a BclI site are added to said restriction site bank.

28. A process according to claim 25, further comprising:
(i) after step (b) but before step (c), the step (b') of deleting a segment of said restriction bank which contains said HincII site in the region between said BglII and AvaI sites of said restriction site bank while retaining the XbaI and PvuII sites in said region, and
(ii) after step (c), the step (d) of substituting the deleted segment for the BglII-AvaI region of said EcoRI-AvaI segment fused to said restriction site bank.

29. A process according to claim 26, further comprising:
(i) after step (b) but before step (c), the step (b') of deleting a segment of said restriction bank which contains said HincII site in the region between said BglII and AvaI sites of said restriction site bank while retaining the XbaI and PvuII sites in said region, and
(ii) after step (d), the step (e) of substituting the deleted segment for the BglII-AvaI region of said EcoRI-AvaI segment fused to said restriction site bank.

30. A process according to claim 27, further comprising:
(i) after step (b) but before step (c), the step (b') of deleting a segment of said restriction bank which contains said HincII site in the region between said BglII and AvaI sites of said restriction site bank while retaining the XbaI and PvuII sites in said region, and
(ii) after step (d), the step (e) of substituting the deleted segment for the BglII-AvaI region of said EcoRI-AvaI segment fused to said restriction site bank.

31. A process according to claim 28, further comprising after step (d) the step (e) of replacing a 910 bp segment between said PstI site and said BglII site in said restriction site bank with a 210 pb PstI-BglII segment derived from plasmid pKC7, whereby an XmaIII site and a BclI site are added to said restriction site bank.

32. A process according to claim 26, further comprising after step (d) the step (e) of deleting an XmaIII restriction site from said PstI-BglIII segment, whereby said restriction site bank has a unique XmaIII site.

33. A process according to claim 27, further comprising after step (d) the step (e) of deleting an XmaIII restriction site from said PstI-BglIII segment, whereby said restriction site bank has a unique XmaIII site.

34. A process according to claim 29, further comprising after step (e) the step (f) of deleting an XmaIII restriction site from said PstI-BglIII segment, whereby said restriction site bank contains unique sites for the restriction enzymes EcoRI, ClaI, HindIII, EcoRV, BamHI, SphI, C, XmaIII, NruI, SacI, KpnI, AsuII, PstI, BalI, BglII, XbaI, PvuII, BalI, MstII and AvaI, where C denotes SalI, AccI, or HincII.

35. A process according to claim 30, further comprising after step (e) the step (f) of deleting an XmaIII restriction site from said PstI-BglIII segment, whereby said restriction site bank contains unique sites for the restriction enzymes EcoRI, ClaI, HindIII, EcoRV, BamHI, SphI, C, XmaIII, NruI, SacI, KpnI, AsuII, PstI, BalI, BglII, XbaI, PvuII, BalI, MstII and AvaI, where C denotes SalI, AccI, or HincII.

36. A process according to claim 32, further comprising:
(i) after step (b) but before step (c), the step (b') of deleting a segment of said restriction bank which contains said HincII site in the region between said BglII and AvaI sites of said restriction site bank while retaining the XbaI and PvuII sites in said region, and
(ii) after step (e), the step (f) of substituting the deleted segment for the BglII-AvaI region of said EcoRI-AvaI segment fused to said restriction site bank.

37. A process according to claim 33, further comprising:
(i) after step (b) but before step (c), the step (b') of deleting a segment of said restriction bank which contains said HincII site in the region between said BglII and AvaI sites of said restriction site bank while retaining the XbaI and PvuII sites in said region, and
(ii) after step (e), the step (f) of substituting the deleted segment for the BglII-AvaI region of said EcoRI-AvaI segment fused to said restriction site bank during step (c).

38. A process according to claim 23, further comprising the step of fusing an XhoI site to the AvaI end of said restriction site bank.

39. A culture of cells transformed with a cloning vehicle comprising a restriction site bank which is the product of a process comprising the steps of (1) digesting the T5 phage genome with HindIII endonuclease into a plurality of fragments and (2) isolating from said plurality the HindIII-L fragment, said restriction bank comprising a first sequence, in the following order, of sites for the restriction enzymes HindIII, Z, KpnI, AsuII, PstI, BglII, XbaI, F, PvuII, BalI, MstII and G, where
Z denotes either a SacI site or a DNA segment lacking a site for a restriction enzyme,
F denotes either a HincII site or a DNA segment lacking a site for a resctriction enzyme, and
G denotes an AvaI site or a XhoI site.

40. A culture according to claim 39, said cells comprising E. coli MM294 cells transformed with plasmid pJRD143.

41. A method cloning DNA, comprising the steps of:
(a) inserting a DNA segment at a predetermined restriction site in a cloning vehicle which comprises a restriction site bank derived from the HindIII-L fragment of bacteriophage T5, said restriction site bank containing at least 10 unique sites for restriction enzymes selected from the group consisting of EcoRI, ClaI, HindIII, EcoRV, BamHI, SphI, Y, XmaIII, NruI, SacI, KpnI, AsuII, PstI, BclI, BglII, XbaI, PvuII, BalI, MstII, AvaI, and XhoI, where Y denotes SalI, AccI, or HincII; and, thereafter, (b) transforming with said cloning vehicle a cell with which said cloning vehicle is compatible, said predetermined restriction site having been selected so that cleavage of said DNA segment by a restriction enzyme recognizing said predetermined restriction site is avoided.

42. A method for producing a selected polypeptide, comprising the steps of:

(a) inserting a DNA segment coding for a polypeptide at a first predetermined restriction site in a vector which comprises a restriction site bank derived from the HindIII-L fragment of bacteriophage T5, said restriction site bank containing at least 10 unique sites for restriction enzymes selected from the group consisting of EcoRI, ClaI, HindIII, EcoRV, BamHI, SphI, Y, XmaIII, NruI, SacI, KpnI, AsuII, PstI, BclI, BglII, XbaI, PvuII, BalI, MstII, AvaI, and XhoI, where Y denotes SalI, AccI, or HincII; and, thereafter, (b) transforming with said vector a cell with which said vector is compatible, said cell being capable of expressing said DNA segment after transformation; and then (c) culturing said cell to produce said polypeptide, said first predetermined restriction site having been selected so that cleavage of said DNA segment by a restriction enzyme recognizing said first predetermined restriction site is avoided.

43. A method according to claim 42, further comprising after step (a) but before step (b) the step of inserting at a second predetermined restriction site in said vector a transcription control sequence said second predetermined restriction site being located upstream from said first predetermined restriction site, relative to the direction said DNA segment is transcribed by said cell.

* * * * *

UNITED STATES PATENT AND TRADEMARK OFFICE
CERTIFICATE OF CORRECTION

PATENT NO. : 4,657,858
DATED : April 14, 1987
INVENTOR(S) : John R.N. Davison

It is certified that error appears in the above—identified patent and that said Letters Patent is hereby corrected as shown below:

On the face of the patent:

Assignee: "Labofina, S.A., Brussels, Fed. Rep. of Germany"

should be:

"Labofina, S.A., Brussels, Belgium"

Signed and Sealed this

Fourteenth Day of June, 1988

*Attest:*

DONALD J. QUIGG

*Attesting Officer*    *Commissioner of Patents and Trademarks*